Figure 1:
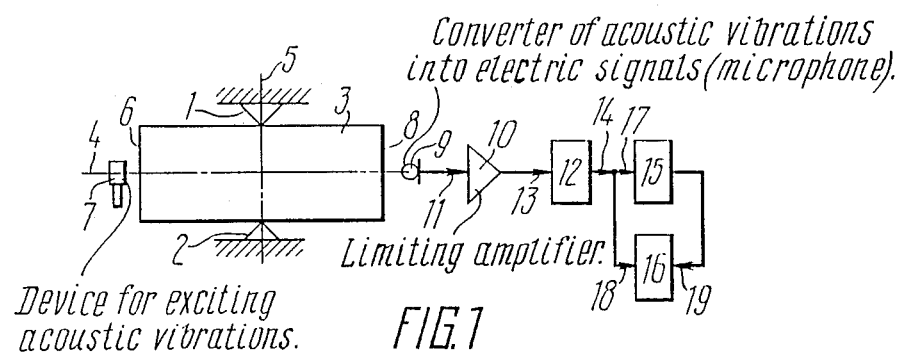

United States Patent [19]
Grebenkin et al.

[11] Patent Number: 4,872,344
[45] Date of Patent: Oct. 10, 1989

[54] METHOD OF NONDESTRUCTIVE QUALITY CONTROL OF CARBON ARTICLES

[75] Inventors: Anatoly F. Grebenkin; Boris A. Glagovsky; Igor B. Moskovenko; Ljudmila P. Lasukova, all of Leningrad, U.S.S.R.

[73] Assignee: Vsesojuzny Nauchno-Issledovatelsky I Proektny Institut Aljuminievoi, Magnievoi I Elektrodnoi, Leningrad, U.S.S.R.

[21] Appl. No.: 153,270
[22] PCT Filed: Nov. 20, 1986
[86] PCT No.: PCT/SU86/00117
§ 371 Date: Nov. 4, 1987
§ 102(e) Date: Nov. 4, 1987
[87] PCT Pub. No.: WO87/05392
PCT Pub. Date: Sep. 11, 1987

[30] Foreign Application Priority Data

Mar. 6, 1986 [SU] U.S.S.R. ............................ 4052258

[51] Int. Cl.$^4$ ........................................... G01N 29/00
[52] U.S. Cl. ........................................... 73/579; 73/597
[58] Field of Search ......................... 73/579, 597, 601

[56] References Cited

U.S. PATENT DOCUMENTS 4,326,417  4/1982  Migliori ............................... 73/601

FOREIGN PATENT DOCUMENTS 1188637  10/1985  U.S.S.R. .

OTHER PUBLICATIONS

V. N. Boganik, "Metody Operativnogo Obobschenia Promyslovogeofizicheskoi Informatsii", 1983. (Nedra Publ., Moscow) pp. 109–110.
L. I. Pomenants et al., "Promyslovo Geofizicheskaya Apparatura; Oborudovaine", 1966.(Nedra Publ., Moscow), p.134.
"Geophysical Methods of Investigation of Oil and Gas Wells", (Nedra Publishers, Moscow) 1981, pp. 32–33, 160–161, and 176–179.

Primary Examiner—John Chapman
Attorney, Agent, or Firm—Lilling & Greenspan

[57] ABSTRACT

A method of nondestructive quality control of carbon articles includes the steps of determining the rate of propagation of excited acoustic vibrations in each carbon article (3) of a group of carbon articles and in a specimen cut out from at least one carbon article (3). Then there are selected the carbon articles (3) with the lowest and highest determined rates of propagation of the acoustic vibrations, and "n" specimens are cut out from them longitudinally of the specimens, and "m" specimens are cut out from them across their longitudinal axes. The averaged values of the rate of propagation of the acoustic vibrations in these selected cabron articles (3) and of their specific electric resistance are determined, respectively, from expressions:

$$\overline{C}_e = \frac{1}{n+m} \sum_1^{m+n} C_e \text{ and } \overline{\rho} = \frac{1}{n+m} \sum_1^{n+m} \rho.$$

Their linear correlated relationship is plotted to define the range of the values of the specific electric resistance, and, hence, the range of the rate of propagation of the acoustic vibrations in the carbon articles (3), held representative of the quality of the carbon articles (3), and this range of the values of the rate of propagation of the acoustic vibrations is used to select acceptable carbon articles (3).

1 Claim, 1 Drawing Sheet

U.S. Patent  Oct. 10, 1989  4,872,344

METHOD OF NONDESTRUCTIVE QUALITY CONTROL OF CARBON ARTICLES

BACKGROUND OF THE INVENTION

1. Field of the Invention

The present invention relates to methods of testing of carbon articles, and more particularly it relates to methods of nondestructive quality control of carbon articles.

2. Description of the Prior Art

There is known a method of nondestructive quality control of carbon articles (see, for example, "Geophysical Methods of Investigation of Oil and Gas Wells" edited by L. I. Pomeranets, Moscos, NEDRA Publishers, 1981, pp. 32-43, 160-186, in Russian). This method includes the steps of exciting acoustic vibrations in each carbon article taken from a group of carbon articles, and in a specimen cut out from at least one carbon article, converting acoustic vibrations in each carbon article and in the specimen into an electric signal having a frequency corresponding to the frequency of the acoustic vibrations, measuring the frequency of the electric signal to determine the frequency of the acoustic vibrations in the specimen and in the corresponding carbon article, determining the rate of propagation of the acoustic vibrations in each carbon article, measuring the specific electric resistance of the carbon articles, establishing the relationship of the rate of propagation of the acoustic vibrations in a carbon article to its specific resistance, determining the range of the rate of propagation of the acoustic vibrations from the range of predetermined values of the specific resistance, and selecting the carbon articles within the range of the rate of propagation of the acoustic vibrations, held representative of the quality of the carbon articles.

According to this method, the measuring of the specific electric resistance of the carbon articles is performed with a quantity of the carbon articles which is commensurate with the quantity of the articles in the whole lot of group, and the relationship of the rate of propagation of the acoustic vibrations in a carbon to its specific electric resistance is established for each carbon article in the lot.

It can be seen, however, that in this method the necessity of measuring the specific electric resistance of each carbon article, followed by establishing the relationship of the rate of propagation of the acoustic vibrations in the carbon article to its specific electric resistance cannot but decrease the rate of quality control of carbon articles and step up the input of labour and effort into the quality control procedure.

SUMMARY OF THE INVENTION

The present invention is to create a method of nondestructive quality control of carbon articles wherein the rate of propagation of acoustic vibrations, the specific electric resistance of the carbon articles and their relationship should be determined in a way providing for speeding up the rate of quality control of carbon articles and lowering the labour and effort input into the quality control procedure.

This is attained in a method of nondestructive quality control of carbon articles, including the steps of exciting acoustic vibrations in each carbon article taken from a group of carbon articles and in a specimen cut out from at least one carbon article, converting the acoustic vibrations in each carbon article and in the specimen into an electric signal having a frequency corresponding to the frequency of the acoustic vibrations, measuring the frequency of the electric signal to determine the frequency of the acoustic vibrations in a carbon article and in the specimen, determining the rate of propagation of the acoustic vibrations in the specimen and in the corresponding carbon article, determining the rate of propagation of the acoustic vibrations in each carbon article, measuring the specific electric resistance of the carbon articles, establishing the relationship of the rate of propagation of the acoustic vibrations in a carbon article to its specific electric resistance, determining the range of the rate of propagation of the acoustic vibrations from the range of predetermined values of the specific electric resistance, and selecting carbon articles falling within the range of the rate of propagation of the acoustic vibrations, held representative of the quality of a carbon article. In accordance with the present invention, after the determination of the rate of propagation of the acoustic vibrations in each carbon article, there are selected from the group of carbon articles at least one carbon article with the lowest determined rate of propagation of the acoustic vibrations therein and at least one carbon article with the highest determined rate of propagation of the acoustic vibrations therein. This is followed by the steps of cutting out from each thus selected carbon article "n" specimens longitudinally thereof and "m" specimens across the longitudinal axis thereof, exciting acoustic vibrations in each one of said "n" and "m" specimens, converting the acoustic vibrations in each one of said "n" and "m" specimens into an electric signal having a frequency corresponding to the frequency of the acoustic vibrations, measuring the frequency of the electric signal to determine the frequency of the acoustic vibrations in each one of said "n" and "m" specimens, determining successively the rate of propagation of the acoustic vibrations in and the specific electric resistance of each one of said "n" and "m" specimens, determining the rate of propagation of the acoustic vibrations in the selected carbon articles by finding its averaged value therein from an expression:

$$\overline{C_e} = \frac{1}{n+m} \sum_{1}^{n+m} C_e,$$

where $C_e$ is the rte of propagation of the acoustic vibrations, the determination of the specific electric resistance of the carbon articles in the group. The quantity is defined by the number of the selected carbon articles, being effected by determination of its averaged value from an expression:

$$\overline{\rho} = \frac{1}{n+m} \sum_{1}^{n+m} \rho,$$

where $\rho$ is the specific electric resistance, and the establishment of the relationship of the rate of propagation of the acoustic vibrations in a carbon article to its specific electric resistance being effected by finding the linear correlated relationship of the averaged value of the rate of propagation of the acoustic vibrations in the selected carbon articles to the averaged value of their specific electric resistance.

The present invention allows for measuring the specific electric resistance in a substantially smaller number of carbon articles, which speeds up quality control procedure and also reduces the input of labour into this procedure.

Furthermore, the present invention provides for avoiding non-uniformity in determination of the specific electric resistance in a carbon article, as a whole, which enhances the accuracy of quality control.

BRIEF DESCRIPTION OF ACCOMPANYING DRAWINGS

Figure 2:
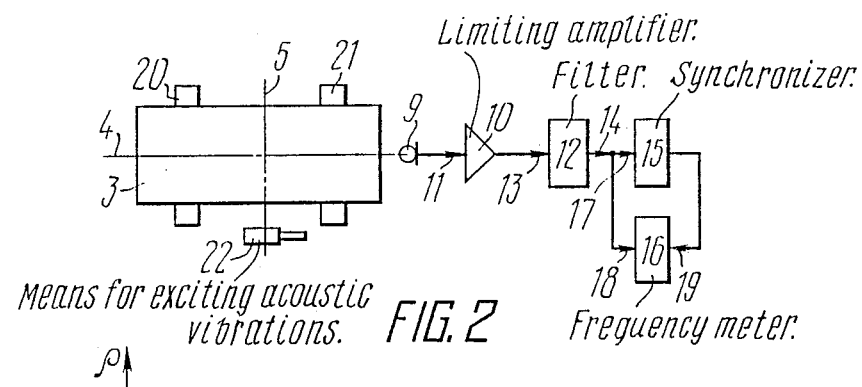
Figure 3:
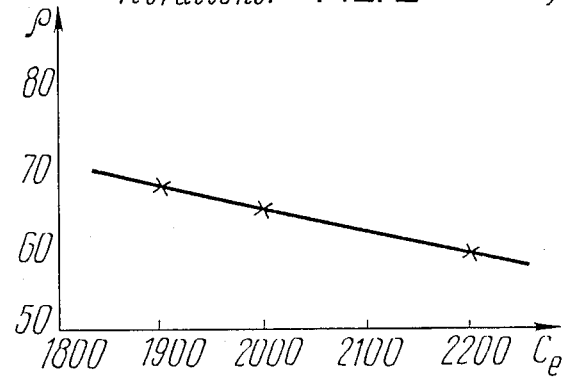

The present invention will be further described in connection with examples of implementation of the presently disclosed method, with reference to the accompanying schematic drawings, wherein:

FIG. 1 is a functional block diagram of an apparatus for nondestructive quality control of carbon articles, implementing the disclosed method;

FIG. 2 is a functional block diagram of a modified apparatus for nondestructive quality control of carbon articles of greater lengths, implementing the disclosed method; and FIG. 3 illustrates a chart of correlated relationship of the specific electric resistance of carbon articles to the rate of propagation of acoustic vibrations therein, according to the method of nondestructive quality control of carbon articles of the present invention.

DESCRIPTION OF THE PREFERRED METHOD

The disclosed method of nondestructive quality control of carbon articles includes exciting acoustic vibrations in each carbon article of a group of carbon articles and in a specimen cut out from at least one of the carbon articles, converting the acoustic vibrations in each carbon article and in the specimen into an electric signal having a frequency corresponding to the frequency of the acoustic vibrations, measuring the frequency of the electric signal to determine the frequency of the acoustic vibrations in a carbon article and in the specimen, and determining the rate of propagation of the acoustic vibrations in the specimen and in the corresponding carbon article. Then the shape of form factor of the carbon articles in established, and the rate of propagation of the acoustic vibrations in each carbon article is determined. Then, there are selected from the group of the carbon articles at least one carbon article with the lowest determined rate of propagation of the acoustic vibrations therein and at least one carbon article with the highest determined rate of propagation of the acoustic vibrations therein; and out of each thus selected carbon article are cut "n" specimens longitudinally thereof and "m" specimens across the longitudinal axis thereof, and acoustic vibrations are excited in each one of said "n" and "m" specimens. Then the acoustic vibrations in each one of said "n" and "m" specimens are converted into an electric signal having a frequency corresponding to the frequency of the acoustic vibrations, the value of the frequency of the electric signal is measured to determine the frequency of the acoustic vibrations in each one of said "n" and "m" specimens, the rate of propagation of the acoustic vibrations in and the specific electric resistance of each one of said "n" and "m" specimens are successively determined, the averaged value of the rate of propagation of the acoustic vibrations in the selected carbon articles is determined from an expression:

$$\overline{C}_e = \frac{1}{n+m} \sum_1^{n+m} C_e,$$

where $C_e$ is the rate of propagation of the acoustic vibrations, and the rate of propagation of the acoustic vibrations in each carbon article is determined. This is followed by determining the averaged value of the specific electric resistance of the selected carbon articles from an expression:

$$\overline{p} = \frac{1}{n+m} \sum_1^{n+m} p,$$

where $p$ is the specific electric resistance. The correlated linear relationship of the averaged value of the rate of propagation of the acoustic vibrations in the selected carbon articles to the averaged value of their specific electric resistance is found, and a range of the rate of propagation of the acoustic vibrations is determined from a range of the values of the specific electric resistance, and carbon articles are picked up within this range of the rates of propagation of the acoustic vibrations, held representative of the quality of the carbon articles.

The disclosed method of nondestructive quality control of carbon articles can be carried out in a known apparatus for quality control of carbon articles (see, for example, A. A. Botaki, V. L. Ulyanov, A. V. Sharko "Ultrasonic Testing of Strength Characteristics of Structural Materials", Moscow, MASHINOSTROENIE Publishers, 1983, pp. 35–36, in Russian), comprising coaxially arranged supports 1 (FIG. 1) and 2 in which a tested carbon article 3 is set with its longitudinal axis 4 extending normally to the axes of the supports 1 and 2 and its transverse axis 5 passing through the supports 1 and 2. A device 7 for exciting acoustic vibrations (hereinafter referred to as the striker 7) is positioned at the end face 6 of the article 3, and at its opposite end face 8 is positioned a converter 9 (a transducer) of acoustic vibrations into an electric signal. A limiting amplifier 10 is connected to the converter 9 by its input 11, and a filter 12 is connected to the limiting amplifier 10 by its input 13. Connected to the output 14 of the filter 12 are a synchronizer 15 and a frequency meter 16 by their respective inputs 17 and 18, the other input 19 of the frequency meter 16 being connected to the synchronizer 15. The converter 9 of acoustic vibrations can be in the form of a generally known dynamic microphone 9 (see, for example, B. A. Glagovski, I. B. Moskovenko "Low-Frequency Acoustic Methods of Testing in Engineering", Leningrad, MASHINOSTROENIE Publishers, 1977, p. 153, in Russian), and the frequency meter 16 can be in the form of a digital electronic frequency meter 16 (see, for example, op.cit. B. A. Glagovski, I. B. Moskovenko "Low-Frequency Acoustic Methods of Testing in Engineering", p. 153).

A modified design of the broadly known apparatus for nondestructive quality control of carbon articles, capable of carrying out the disclosed method with articles of greater lengths, comprises supports 20 (FIG. 2) and 21 successively arranged in front of the converter 9 of acoustic vibrations in parallelism with the transverse axis 5 of the article 3. The means for exciting acoustic vibrations in this embodiment—a striker 22—is arranged intermediate and equidistant from the supports 20 and 21. The rest of the design of the apparatus schematically illustrated in FIG. 2 is similar to that of the above described apparatus illustrated in FIG. 1.

According to the disclosed method, the known apparatus for nondestructive quality control of carbon articles is operated, as follows.

As the end face 6 (FIG. 1) if the carbon article is hit by the striker 7, acoustic vibrations are excited in the article 3 and sensed by the dynamic microphone 9 which converts the acoustic vibrations into an electric signal fed to the input of the limiting amplifier 10. The limiting function of the amplifier 10 is to ignore the effect of the force of the impact delivered to the article 3 by the striker 7. The electric signal amplified by the limiting amplifier 10 is fed to the input 13 of the filter 12 whose function is to cut off the period of the transition process, to eliminate the influence of external noise on the ensuing process of measuring the frequency of the electric signal coming to the input 13 from the microphone 9, and to extract from this signal a frequency corresponding to the frequency of the acoustic vibrations in the article 3. The frequency signal is fed from the output 14 of the filter 12 to the input 17 of the synchronizer 15 and to the input 18 of the digital frequency meter 16. The synchronizer 15 generates a triggering pulse fed to the input 19 of the frequency meter 16, and the latter measures the frequency of the acoustic vibrations of the article 3. Thus, the value of the frequency measured by the frequency meter 16 is held to be the value of the frequency of the acoustic vibrations of the carbon article 3. Each measured value of the frequency of the acoustic vibrations of the article 3 is retained on the indicator of the frequency meter 16 until a new signal is sensed by the microphone 9.

In case of articles of relatively great lengths, it is preferable to excite flexural acoustic vibrations. So, the striker 22 (FIG. 2) hits a side of the article 3. Thus excited, the acoustic vibrations propagate along the transverse axis 5 of the carbon article 3 and are sensed by the microphone 9. The rest of the operation of the apparatus of FIG. 2 is similar to that of the operation of the apparatus illustrated in FIG. 1.

EXAMPLE

A production lot of carbon anode blocks totalling 200 pieces was tested for quality control. Measurements yielded the values of $C_e$ in a range from 1900 to 2200 m/s. Out of the blocks with $C_{e\ min}=1900$ m/s and $C_{e\ max}=2200$ m/s were cut specimens of a standard size (cylinders 36 mm in diameter, 100 mm long); three specimens along the longitudinal axis 3 and three specimens along the transverse axis 5. Using generally employed techniques, the values of specific electric resistance $\rho$ were measured for these specimens. The values obtained with the specimens cut out from the article 3 with $C_{3\ min}=1900$ m/s were:

$$\rho_{1\ max} = 67.8\ \frac{Ohm \cdot mm^2}{m}; \quad \rho_{2\ max} = 67.6\ \frac{Ohm \cdot mm^2}{m};$$

$$\rho_{3\ max} = 68.2\ \frac{Ohm \cdot mm^2}{m}; \quad \rho_{4\ max} = 68.3\ \frac{Ohm \cdot mm^2}{m};$$

$$\rho_{5\ max} = 67.9\ \frac{Ohm \cdot mm^2}{m}; \quad \rho_{6\ max} = 68.5\ \frac{Ohm \cdot mm^2}{m};$$

Hence, the averaged specific electric resistance $\bar{\rho}$ for the article 3 with $C_3 = 1900$ m/s was found from the expression $$\rho_{aver.\ max} = \bar{\rho}_{max} = 1/6 \sum_{1}^{6} \rho_i = 68.05 \approx 68.1\ \frac{Ohm \cdot mm^2}{m}.$$

Then the frequency of the acoustic vibrations in each specimen was measured, and the values of $C_e$ in the specimens were determined from the frequencies obtained by the measurements:

$C_{e1\ min}=1890$ m/s; $C_{e2\ min}=1930$ ,/s; $C_{e3\ min}=1920$ m/s;

$C_{e3\ min}=1860$ m/s; $C_{e5\ min}=1880$ m/s; $C_{e6\ min}=1890$ m/s.

Hence, the averaged rate of propagation of the acoustic oscillations for the article 3 was found from the expression:

$$\bar{C}_{e\ min} = 1/6 \sum_{1}^{6} C_{ei} = 1895\ m/s \approx 1900\ m/s.$$

In a similar procedure were found the values of $\bar{\rho}_{min}$ and $\bar{C}_{3\ max}$ for the six specimens cut out from the article 3 with $C_{e\ max}=2200$ m/s;

$$\bar{\rho}_{min} = 60.1\ \frac{Ohm \cdot mm^2}{m};$$

$$\bar{C}_{e\ max} = 2210\ m/s.$$

From the obtained values $\bar{\rho}_{max}$, $\bar{C}_{e\ min}$ and $\bar{\rho}_{min}$, $\bar{C}_{e\ max}$ was plotted a chart of correlated relationship of $\rho$ to $C_e$, illustrated in FIG. 3 where the X-axis is calibrated in the units of measurement of $C_3$ (m/s), and the Y-axis is calibrated in the measurement units of $\rho(Ohm.mm^2/m)$. Using this chart, the threshold values of $C_e$ corresponding to the threshold permissible values of $\rho$ were established:

$$C_{e\ max} = 2200\ m/s\ \text{with}\ \rho_{min} = 60\ \frac{Ohm \cdot mm^2}{m};$$

$$C_{e\ min} = 2000\ m/s\ \text{with}\ \rho_{max} = 65\ \frac{Ohm \cdot mm^2}{m}.$$

Using this criterion, those of the articles that had values $C_e > C_{e\ max}$ or $C_e < C_{e\ min}$ were rejected as defective.

The whole quality control procedure took 2 hours, which was less than one half of the time required for carrying out quality control of identical carbon articles according to the method of the prior art, thus attesting to a substantially speeded up quality control procedure.

Moreover, the plotting of the chart expressing the relationship of $\rho$ to $C_e$ in accordance with the disclosed method substantially simiplies the procedure of processing the measurements obtained, which, in its turn, reduces the input of labour into the quality control procedure.

Furthermore, the present invention provides for upgrading the quality of carbon articles passing the control procedure, which brings down their consumption in operation and enhances their performance reliability.

The invention can be employed in the manufacture of carbon articles, e.g. those used in electrolytic production of aluminum and also in other technologies of ferrous and nonferrous metallurgy, in chemistry and in the manufacture of abrasive products.

We claim:

1. A method of nondestructive quality control of carbon articles, comprising the steps of exciting acoustic vibrations in each carbon article taken from a group of carbon articles and in a specimen cut out from at least one carbon article, converting the acoustic vibrations in each carbon article and in the specimen into an electric signal having a frequency corresponding to the frequency of the acoustic vibrations, measuring the frequency of the electric signal to determine the frequency of the acoustic vibrations in each carbon article and in the specimen, determining the rate of propagation of the acoustic vibrations in the specimen and in the corresponding carbon article, determining the rate of propagation of the acoustic vibrations in each carbon article, measuring the specific electric resistance of selected carbon articles, establishing the relationship of the rate of propagation of the acoustic vibrations in a carbon article to its specific electric resistance, determining the range of the rate of propagation of the acoustic vibrations from the range of predetermined values of the specific electric resistance, and selecting carbon articles falling within the range of the rate of propagation of acoustic vibrations, held representative of the quality of a carbon article, wherein after the determination of the rate of propagation of the acoustic vibrations in each carbon article (3), there are selected from the group of carbon articles at least one carbon article (3) with the lowest determined rate of propagation of the acoustic vibrations therein and at least one carbon article (3) with the highest determined rate of propagation of the acoustic vibrations therein, followed by cutting out from each thus selected carbon article (3) "n" specimens longitudinally thereof and "m" specimens across the longitudinal axis thereof, exciting acoustic vibrations in each of said "n" and "m" specimens, converting acoustic vibrations in each one of said "n" and "m" specimens into an electric signal having a frequency corresponding to the frequency of the acoustic vibrations, measuring the frequency of the electric signal to determine the frequency of the acoustic vibrations in each one of said "n" and "m" specimens, determining successively the rate of propagation of acoustic vibrations in and the specific electric resistance of each one of said "n" and "m" specimens, determining the rate of propagation of acoustic vibrations in said selected carbon articles (3) by finding its averaged value therein from an expression:

$$\overline{C}_e = \frac{1}{n+m} \sum_1^{n+m} C_e,$$

where $C_e$ is the rate of propagation of acoustic vibrations, the specific electric resistance of carbon articles in the group, of which the quantity is defined by the number of said selected carbon articles (3), is determined by finding its averaged value from an expression:

$$\overline{\rho} = \frac{1}{n+m} \sum_1^{n+m} \rho,$$

where $\rho$ is the specific electric resistance, and the establishment of the relationship of the rate of propagation of the acoustic vibrations in a carbon article (3) to its specific electric resistance is effected by finding the linear correlated relationship of the averaged value of the rate of propagation of the acoustic vibrations in said selected carbon articles (3) to the averaged value of their specific electric resistance.

* * * * *